US008632518B2

(12) United States Patent
La Von et al.

(10) Patent No.: US 8,632,518 B2
(45) Date of Patent: Jan. 21, 2014

(54) ABSORBENT ARTICLES AND METHOD FOR MANUFACTURING SAME

(75) Inventors: Gary Dean La Von, Liberty Township, OH (US); Thomas Henrich, Montgomery, OH (US)

(73) Assignee: The Procter & Gamble Plaza, Cincinnati, OH (US)

( * ) Notice: Subject to any disclaimer, the term of this patent is extended or adjusted under 35 U.S.C. 154(b) by 452 days.

(21) Appl. No.: 12/624,822

(22) Filed: Nov. 24, 2009

(65) Prior Publication Data
US 2011/0125124 A1   May 26, 2011

(51) Int. Cl.
*A61F 13/15*   (2006.01)

(52) U.S. Cl.
USPC ..................... 604/394; 604/385.11

(58) Field of Classification Search
USPC ........... 604/385.02, 385.201, 385.11, 385.13, 604/385.29, 389, 394
See application file for complete search history.

(56) References Cited

U.S. PATENT DOCUMENTS

| | | | |
|---|---|---|---|
| 3,860,003 A | | 1/1975 | Buell |
| 4,122,552 A | * | 10/1978 | Tedford ............................ 2/402 |
| 4,326,528 A | * | 4/1982 | Ryan et al. ............... 604/385.26 |
| 4,610,678 A | | 9/1986 | Weisman et al. |
| 4,630,320 A | * | 12/1986 | Van Gompel ..................... 2/406 |
| 4,834,735 A | | 5/1989 | Alemany et al. |
| 4,888,231 A | | 12/1989 | Angstadt |
| 4,917,675 A | * | 4/1990 | Taylor et al. ............. 604/385.02 |
| 5,037,416 A | | 8/1991 | Allen et al. |
| 5,151,092 A | | 9/1992 | Buell et al. |
| 5,260,345 A | | 11/1993 | DesMarais et al. |
| 5,269,775 A | | 12/1993 | Freeland et al. |
| 5,358,499 A | | 10/1994 | Seidy |
| 5,387,207 A | | 2/1995 | Dyer et al. |
| 5,397,316 A | | 3/1995 | LaVon et al. |
| 5,554,145 A | | 9/1996 | Roe et al. |
| H1602 H | * | 10/1996 | Brock ............................ 604/387 |
| 5,569,234 A | | 10/1996 | Buell et al. |
| 5,571,096 A | | 11/1996 | Dobrin et al. |
| 5,704,929 A | * | 1/1998 | Bien ........................ 604/385.23 |
| 5,993,430 A | * | 11/1999 | Gossens et al. .......... 604/385.02 |
| 6,004,306 A | | 12/1999 | Robles et al. |
| 6,156,424 A | | 12/2000 | Taylor |
| 6,524,290 B2 | * | 2/2003 | Motta et al. .............. 604/385.01 |
| 6,994,696 B2 | | 2/2006 | Suga |

(Continued)

FOREIGN PATENT DOCUMENTS

GB   2 303 045 A   2/1997
WO   WO 95/16746 A1   6/1995

OTHER PUBLICATIONS

PCT International Search Report and Written Opinion dated Jan. 28, 2011, 10 pages.

(Continued)

*Primary Examiner* — Jackie Ho
*Assistant Examiner* — Peter S Vasat
(74) *Attorney, Agent, or Firm* — Charles R. Matson; Abbey A. Lopez

(57) ABSTRACT

An absorbent product comprises a seal along one or more edges. The seal may be formed using a cohesive or selective adhesive. The seal prevents contamination of the wearer-facing surface of an individual absorbent product without requiring an overwrap or other individual unit packaging. The absorbent product may also comprise one or more removable trim regions for sealing and shaping the absorbent product.

20 Claims, 10 Drawing Sheets

(56) References Cited

U.S. PATENT DOCUMENTS

| | | |
|---|---|---|
| 7,427,277 B2 | 9/2008 | Woltman et al. |
| 2002/0032427 A1* | 3/2002 | Schmitz et al. .......... 604/385.11 |
| 2005/0131371 A1* | 6/2005 | Fell et al. ................. 604/385.02 |
| 2005/0177127 A1 | 8/2005 | Ashton et al. |
| 2006/0282057 A1 | 12/2006 | Otsubo et al. |
| 2008/0107861 A1* | 5/2008 | Dalal et al. ..................... 428/99 |

OTHER PUBLICATIONS

U.S. Appl. No. 12/624,851, filed Nov. 24, 2009, Schneider, et al.

\* cited by examiner

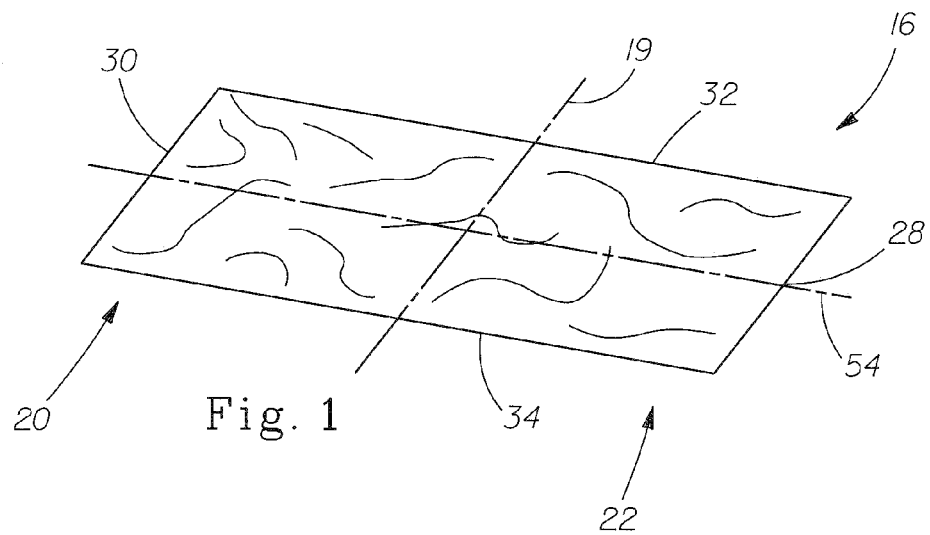
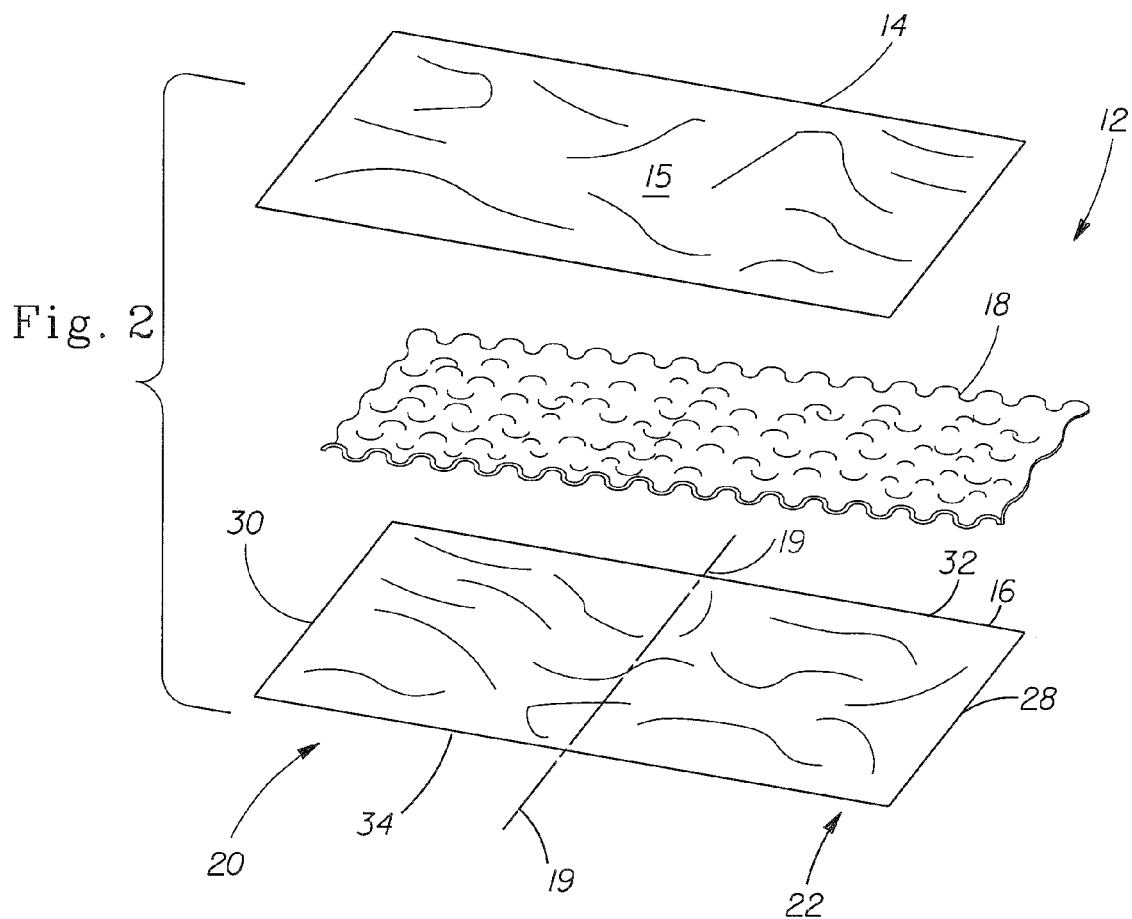

ABSORBENT ARTICLES AND METHOD FOR MANUFACTURING SAME

FIELD OF THE INVENTION

The present disclosure generally relates to absorbent articles and methods for manufacturing the same, and more particularly relates to absorbent articles packaged for individual sale and methods for manufacturing the same.

BACKGROUND OF THE INVENTION

Absorbent articles, such as diapers, for example, can be sold individually. Although typically sold in packages containing multiple absorbent articles, it may be desirable to purchase a single absorbent article under certain circumstances. For example, individual articles may be desirable as unplanned or "emergency" purchases from a vending machine or convenience store; when a consumer wishes to experiment with a new size, brand, or style of absorbent article; or in locales where the average income may make bulk packages price prohibitive for many consumers. In such instances, a retailer may open a package of the absorbent articles and then sell individual absorbent articles to consumers.

One common function of the packaging or overwrap for a package of multiple absorbent articles is keeping the absorbent articles clean and dry prior to purchase and use. For products such as bandages, diapers, catamenial napkins, and other absorbent articles which may be used in proximity to tender or disrupted skin, a contaminated surface may compromise product performance; introduce undesirable irritants to the skin, mucosal membranes, or wound adjacent the absorbent article during use; or present an undesirable "dirty" appearance that may deter purchase or use. For these and other reasons, absorbent articles intended to be carried for later application or to be sold individually are often packaged in individual overwraps. However, these overwraps add cost and bulk to the articles, and generate extra waste when the overwrap is removed and discarded.

It would be desirable to provide an absorbent article suitable for individual sales which has interior, skin-contacting surfaces protected from contamination without an extra wrapper or package for each individual article.

SUMMARY OF THE INVENTION

In some embodiments, the invention comprises an absorbent product comprising a chassis. The chassis comprises a topsheet having a wearer-facing surface, a backsheet having a garment-facing surface, an absorbent core disposed between the topsheet and the backsheet, a first longitudinal side edge, a second longitudinal side edge, a first lateral end edge, a second lateral end edge, and a first lateral axis. The absorbent product is folded about the first lateral axis such that the first lateral end edge and the second lateral end edge are adjacent to each other and the chassis has a first portion on one side of the first lateral axis and a second portion on the other side of the first lateral axis. The absorbent product further comprises a first seal between the first lateral end edge and the second lateral end edge; a second seal between the first longitudinal side edge in the first portion of the chassis and the first longitudinal side edge in the second portion of the chassis; and a third seal between the second longitudinal side edge in the first portion of the chassis and the second longitudinal side edge in the second portion of the chassis. The first seal forms a waist opening when at least a portion of the first seal is disrupted, and the second and third seals form leg openings when at least a portion of the second and third seals are disrupted.

BRIEF DESCRIPTION OF DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein:

FIG. 1 is a perspective view of a backsheet used in making an absorbent product;

FIG. 2 is a perspective view of the backsheet of FIG. 1, a topsheet, and an absorbent core used in making an absorbent product;

FIG. 7A is a perspective view of an absorbent product with the longitudinal edges folded in;

DETAILED DESCRIPTION OF THE INVENTION

Figure 3:
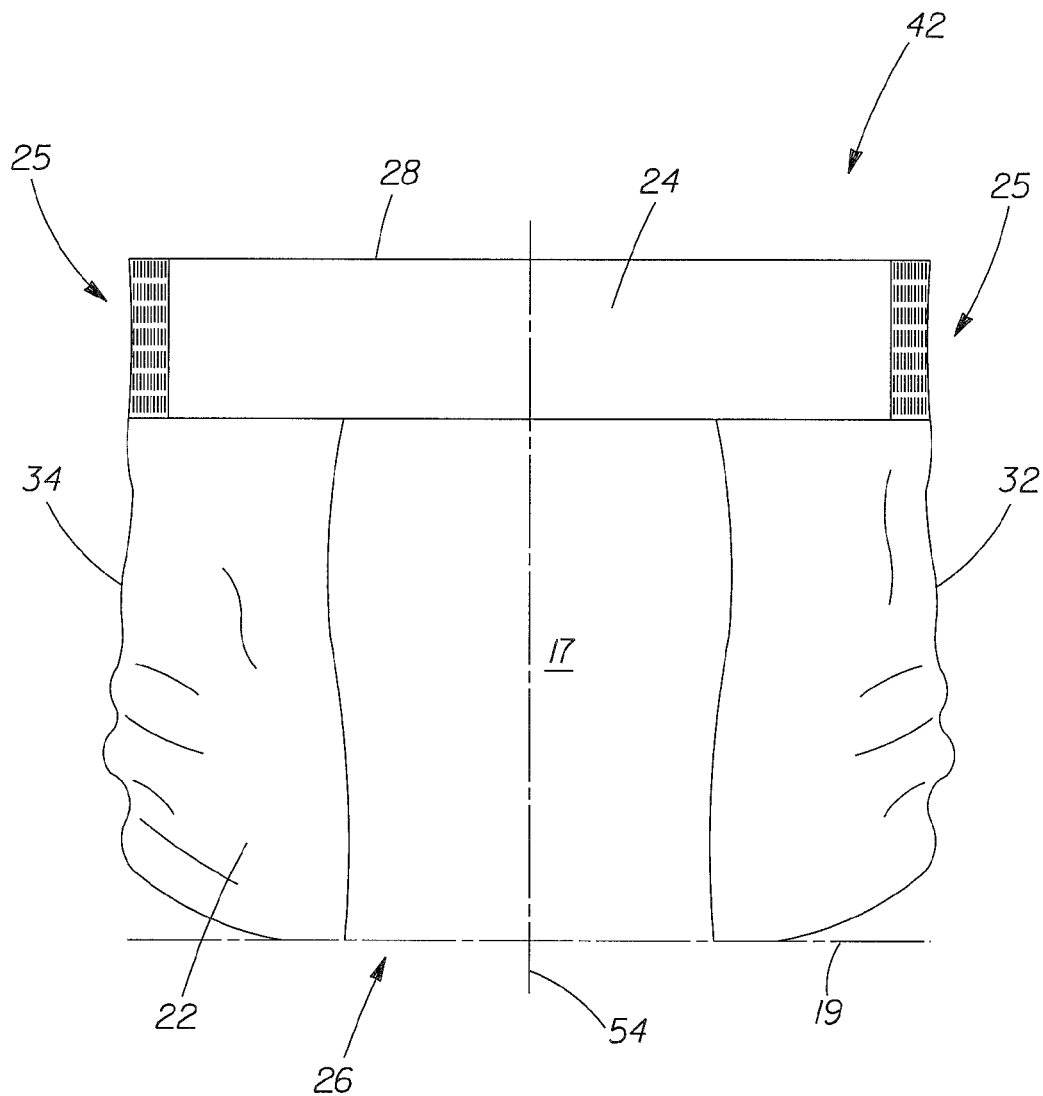
FIG. 3 is a front view of an absorbent product folded about a lateral axis.
Figure 4:
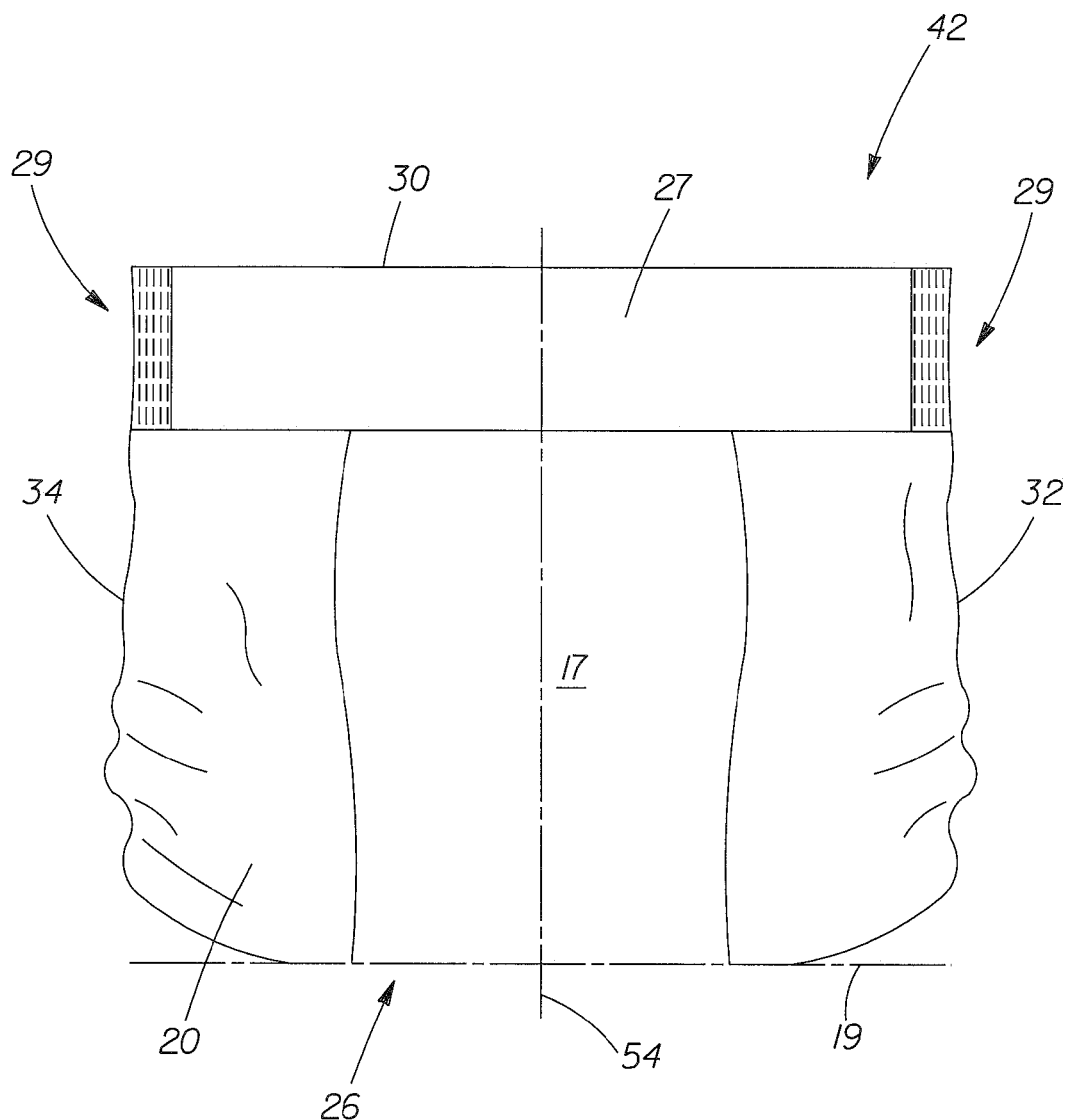
FIG. 4 is a rear view of the absorbent product of FIG. 3.

Various non-limiting embodiments of the present disclosure will now be described to provide an overall understanding of the principles of the structure, function, manufacture, and use of the apparatuses and methods disclosed herein. One or more examples of these non-limiting embodiments are illustrated in the accompanying drawings. It is to be appreciated that the apparatuses and methods specifically described herein and illustrated in the accompanying drawings are non-limiting example embodiments and that the scope of the various non-limiting embodiments of the present disclosure are defined solely by the claims. The features illustrated or described in connection with one non-limiting embodiment may be combined with the features of other non-limiting embodiments. It is also to be appreciated that such features can be combined with features of the absorbent articles and methods of manufacture disclosed in the U.S. patent application entitled "ABSORBENT ARTICLES AND METHODS FOR MANUFACTURING SAME," filed Nov. 24, 2009, and identified as attorney docket number 11516. Such modifications and variations are intended to be included within the scope of the present disclosure.

As used herein, the terms "typical adhesive" and "traditional adhesive" are interchangeable and refer to an adherent which demonstrates adhesion when applied to another material generally (e.g. the adherend material is not specially selected). Traditional adhesive materials connect to other materials indiscriminately and may stick to a variety of materials. Traditional adhesives are tacky and/or become tacky at certain temperatures. Generally, typical adhesive materials used in disposable absorbent articles demonstrate adhesion either at certain temperatures (such as a hot melt adhesive) or under pressure (a pressure sensitive adhesive).

As used herein, the term "cohesive" refers to a material that demonstrates surface interaction (in terms of connection of one surface to another) when applied to itself or to an analog of itself (i.e., the same or essentially the same material is both the adherent and adherend) at room temperature. An A-A type cohesive material will fasten or form a connection primarily to itself. Generally, such cohesives are substantially non-tacky (such as to skin) at room temperature or while under moderate pressure (e.g., finger pinch pressure).

As used herein, the term "selective adhesive" refers to an adherent which demonstrates surface interaction (in terms of connection of one surface to another) when applied to a specially selected adherend at room temperature. An A-A' type selective adhesive system demonstrates surface interaction where adherent A will stick to adherend A', where A' is a material that is chemically similar to A. An A-B type selective adhesive system demonstrates surface interaction properties where adherent A will stick to a different material, adherend B. The adherend may also be a selective adhesive or cohesive. For example, in an A-A' type selective system, A may also attach to A, and A' may attach to A'. In another example, an A-B type selective adhesive system could also exist where material A may attach to itself or to material B, but material B will not attach to itself. The adherent and adherend of selective adhesives can be non-tacky.

As used herein, the term "contaminant" refers to any substance or object which is not intended to be present on the wearer-facing surface of the product, and may include, but is not limited to, bacteria; insects, rodents, or their droppings; dust; dirt; chemicals; excessive moisture; and the like.

As used herein, the terms "inboard" and "outboard" refer to the position of an object relative to the longitudinal or lateral centerline of an absorbent article. A first object is inboard of a second object if the first object is nearer the longitudinal or lateral centerline than the second object. A first object is outboard of a second object if the first object is farther from the longitudinal or lateral centerline than the second object.

As used herein, the terms "absorbent product" and "absorbent article" refer to different configurations of an article for receiving and containing urine, menses, and/or other bodily exudates, such as diapers, pull-on diapers, training pants, incontinence briefs, sanitary napkins, and the like. An absorbent article is in the final shape and configuration for application to a wearer, although seals or fasteners may need to be adjusted prior to or during application. An absorbent product is an absorbent article which requires additional shaping prior to application, as, for example, by removing a removable trim region, as described below.

As used herein, the terms "sealed" and "joined" refer to different connections between components of an article. A "seal" is frangible and is broken or disrupted to enable some functionality of an article. A "joint" is a connection between parts of the article and is typically not intended to be broken or disrupted during use. For example, a seal may be broken to form a waist opening or leg opening that allows a disposable absorbent article to be fitted to a wearer. A joint may join the backsheet and topsheet of a disposable absorbent article, or join a fastening system to the waist region. A joint may be frangible, but a frangible joint will typically be disrupted or broken at the end of a product's useful life, e.g., to remove a used absorbent article.

Absorbent articles, such as diapers, training diapers, pull-up pants, incontinence briefs, and undergarments, for example, may be sold individually. A retailer may open a package of multiple absorbent articles, and sell the absorbent articles individually. To protect the individual absorbent articles from contaminants after the package is opened, individual absorbent products may be configured to maintain wearer facing surfaces of the individual absorbent articles in a sanitary condition prior to use. In one embodiment, the individual absorbent products may be sealed about at least a portion of an outer perimeter to prevent contaminants from contacting the wearer-facing surfaces of the product prior to use.

In various embodiments of the present disclosure, referring to FIGS. 1-4, absorbent article 42, which can be individually sealed, may comprise chassis 12, which may form a main body of absorbent article 42. Chassis 12 may comprise an outer covering including liquid pervious topsheet 14 and liquid impervious backsheet 16. Topsheet 14 may comprise a wearer facing surface 15 and backsheet 16 may comprise garment facing surface 17. Chassis 12 may comprise absorbent core 18 positioned intermediate topsheet 14 and backsheet 16. Stated another way, absorbent core 18 may be sandwiched intermediate topsheet 14 and backsheet 16, as shown in FIG. 2. In some embodiments, chassis 12 may be folded about lateral axis 19 such that first portion 20 of chassis 12 may be positioned adjacent to, or substantially adjacent to, second portion 22 of chassis 12. In such an embodiment, first and second portions 20 and 22 may form first waist region 24 comprising laterally opposing ends 25, second waist region 27 comprising laterally opposing ends 29, and crotch region 26 longitudinally intermediate first and second waist regions 24 and 27. In some embodiments, first and second waist regions 24 and 27 may comprise elastic elements such that they gather about a waist of a wearer to provide improved fit and containment of urine and other body exudates, for example. Crotch region 26 is the portion of absorbent article 42 which is generally positioned between the wearer's legs.

The figures show a highly simplified overview of absorbent article 42 and its components. However, absorbent article 42 may comprise any materials or construction known in the art. While topsheet 14, backsheet 16, and absorbent core 18 may be assembled in a variety of configurations, some exemplary configurations are described generally in U.S. Pat. No. 5,554,145, entitled "Absorbent Article With Multiple Zone Structural Elastic-Like Film Web Extensible Waist Feature", issued to Roe et al. on Sep. 10, 1996; U.S. Pat. No. 5,569,234, entitled "Disposable Pull-On Pant", issued to Buell et al. on Oct. 29, 1996; and U.S. Pat. No. 6,004,306, entitled "Absorbent Article With Multi-Directional Extensible Side Panels", issued to Robles et al. on Dec. 21, 1999.

In some embodiments, topsheet 14 may be fully or partially elasticized or may be foreshortened to provide a void space between topsheet 14 and absorbent core 18. Exemplary structures including elasticized or foreshortened topsheets are described in more detail in U.S. Pat. No. 5,037,416, entitled "Disposable Absorbent Article Having Elastically Extensible Topsheet", issued to Allen et al. on Aug. 6, 1991; and U.S. Pat. No. 5,269,775, entitled "Trisection Topsheets for Disposable Absorbent Articles and Disposable Absorbent Articles Having Such Trisection Topsheets", issued to Freeland et al. on Dec. 14, 1993.

Absorbent core 18 may comprise any absorbent material that is generally compressible, conformable, non-irritating to the wearer's skin, and capable of absorbing and retaining liquids, such as urine and other body exudates. Absorbent core 18 may comprise a wide variety of liquid-absorbent materials commonly used in disposable diapers and other absorbent articles, such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. Absorbent core 18 may further comprise minor amounts (typically less than 10%) of non-liquid absorbent materials, such as adhesives, waxes, oils, and the like, for example.

Exemplary absorbent structures for use in absorbent core 18 are described in U.S. Pat. No. 4,610,678, entitled "High-Density Absorbent Structures", issued to Weisman et al. on Sep. 9, 1986; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231, entitled "Absorbent Core Having A Dusting Layer", issued to Angstadt on Dec. 19, 1989; U.S. Pat. No. 5,260,345, entitled "Absorbent Foam Materials for Aqueous Body Fluids and Absorbent Articles Containing Such Materials", issued to DesMarais et al. on Nov. 9, 1993; and U.S. Pat. No. 5,387,207, entitled "Thin-Unit-Wet Absorbent Foam Materials for Aqueous Body Fluids and Process for Making Same", issued to Dyer et al. on Feb. 7, 1995; and U.S. Pat. No. 5,397,316, entitled "Slitted Absorbent Members for Aqueous Body Fluids Formed of Expandable Absorbent Materials", issued to LaVon et al. on Mar. 14, 1995.

In some embodiments, backsheet 16 may be joined with topsheet 14 at least around portions of the outer perimeters of backsheet 16 and topsheet 14, thereby sandwiching absorbent core 18 therebetween. Backsheet 16 can prevent, or at least inhibit, any exudates absorbed by absorbent core 18 and contained within absorbent article 42 from soiling other external articles that may contact absorbent product 10, such as bed sheets, pants, garments, or undergarments, for example. In some embodiments, backsheet 16 may be substantially impervious to liquids (e.g., urine) and may comprise a laminate of a nonwoven and a thin plastic film, such as a thermoplastic film having a thickness of about 0.012 mm to about 0.051 mm, for example. Suitable backsheet films include those manufactured by Tredegar Industries Inc. of Terre Haute, Ind. and sold under the trade names X15306, X10962, and X10964. Other suitable backsheet materials may include breathable materials that permit vapors to escape through backsheet 16 while still preventing exudates from passing through backsheet 16. Exemplary breathable materials may include materials such as woven webs, nonwoven webs, composite materials such as film-coated nonwoven webs, and microporous films such as manufactured by Mitsui Toatsu Co., of Japan, under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995, in the name of E. I. DuPont. Other breathable backsheets including nonwoven webs and apertured formed films are described in U.S. Pat. No. 5,571,096, entitled "Absorbent Article Having Breathable Side Panels", issued to Dobrin et al. on Nov. 5, 1996.

Absorbent article 42 may also comprise other features as are known in the art, such as front and rear ear panels, waist cap features, elastic, and other suitable components, for example, to provide better fit, better containment, and more pleasant aesthetic characteristics. Various additional features are described in further detail in U.S. Pat. No. 3,860,003, entitled "Contractable Side Portions for Disposable Diaper", issued to Buell on Jan. 14, 1975; and U.S. Pat. No. 5,151,092, entitled "Absorbent Article With Dynamic Elastic Waist Feature Having a Predisposed Resilient Flexural Hinge", issued to Buell et al. on Sep. 29, 1992.

In some embodiments, referring to FIGS. 1-4, backsheet 16 may comprise first laterally extending end edge 28, second laterally extending end edge 30 longitudinally opposed to first laterally extending edge 28, first longitudinally extending side edge 32, and second longitudinally extending side edge 34 laterally opposed to first longitudinally extending side edge 32. Backsheet 16 may have lateral axis 19 and longitudinal centerline 54. First lateral end edge 28 may oppose second lateral end edge 30 such that when first portion 20 of absorbent product 10 is folded about lateral axis 19 over second portion 22 of absorbent product 10, first lateral end edge 28 can be positioned adjacent to, or substantially adjacent to, second lateral end edge 30. In some embodiments, first longitudinal side edge 32 can oppose second longitudinal side edge 34. When first portion 20 of absorbent product 10 is folded over second portion 22 of absorbent product 10 about lateral axis 19, first longitudinal side edge 32 can be folded over itself such that a first portion of the first longitudinal side edge 32 is positioned adjacent to, or substantially adjacent to, a second portion of the first longitudinal side edge 32. Likewise, second longitudinal side edge 34 can be folded over itself such that a first portion of the second longitudinal side edge 34 is positioned adjacent to, or substantially adjacent to, a second portion of second longitudinal side edge 34.

A portion of laterally opposing ends 25 of first waist region 24 may be permanently or refastenably attached to laterally opposing ends 29 of second waist region 27 to form a circular waist opening. Alternately, a fastening system may be provided such that laterally opposing ends 25 and 29 can be operatively joined to one another when absorbent article 42 is applied to a wearer. In some embodiments, absorbent article 42 may include ear panels or side panels, which extend laterally opposing ends 25 and 29 laterally. If ear or side panels are present, the fastening system may be disposed on the ear or side panels rather than, or in addition to, the laterally opposing ends.

Figure 5:
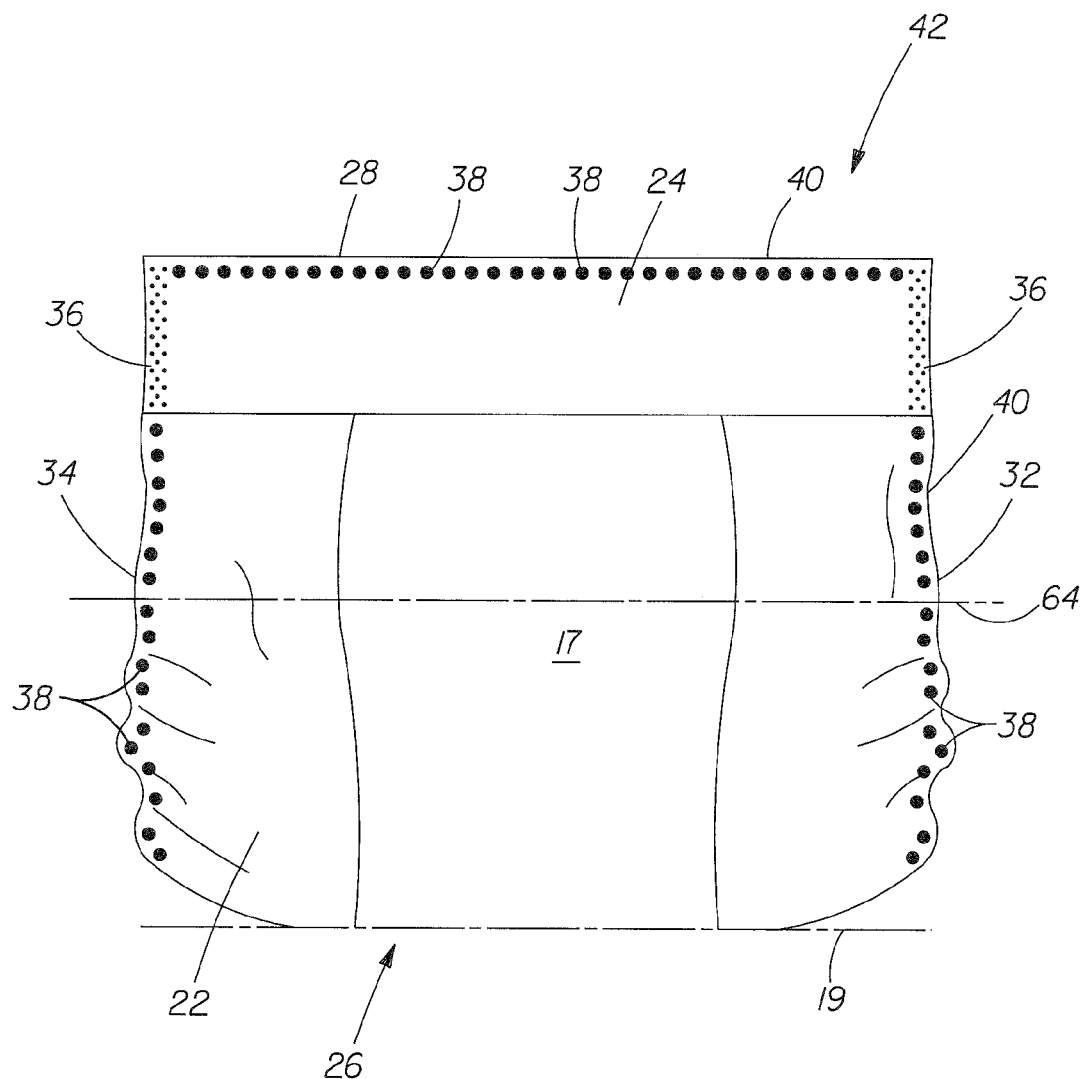
FIG. 5 is a front view of FIG. 3, with various seals formed in the absorbent product.

Further to the above, referring to FIG. 5, seal 38 can be formed partially about outer perimeter 40, or inboard of outer perimeter 40, of absorbent article 42 to seal first portion 20 to second portion 22 and maintain absorbent article 42 in a sanitary condition prior to being positioned on a wearer. To fit absorbent article 42 to a wearer, seal 38 is opened to position the wearer's waist and legs in absorbent article 42. In some embodiments, seal 38 may not extend through crotch region 26 of absorbent article 42, as the wearer-facing surface of crotch region 26 will already be enclosed owing to the folding of first portion 20 over second portion 22 about lateral axis 19. Seal 38 can be formed by applying an adhesive or cohesive near or on the outer perimeter of first portion 20 and/or second portion 22 and then applying pressure to absorbent article 42 to cause the adhesive or cohesive to seal first portion 20 to second portion 22.

If seal 38 comprises an adhesive, the adhesive used may be a selective adhesive or an "A-B" adhesive that adheres preferentially to specific surfaces. In such an embodiment, when the product is opened, it is less likely that the adhesive residue will adhere to the wearer; will adhere to the wearer's undergarments, garments, or bedsheets; will adhere to other parts of the product; or will collect dust and dirt from the wearer's environment. Selective adhesives are described, for example, in U.S. Patent Application Publication No. 2008/0107861, filed Nov. 2, 2007 in the name of Dalal, et al. Exemplary selective adhesive combinations include a styrene block copolymer adherent (such as styrene-isoprene-styrene, styrene-butadiene-styrene, or styrene-isoprene-styrene) with a polypropylene or polyethylene adherend.

Seal 38 may also comprise a cohesive. A cohesive, like a selective adhesive or A-B adhesive, may be selected such that it will not adhere significantly to equipment used during manufacture, or to unintended parts of the product being assembled, and may provide similar benefits in terms of not adhering to the wearer, other surfaces, or dust or dirt from the wearer's environment. Cohesives are described, for example, in U.S. Pat. No. 6,156,424 to Taylor; U.S. Patent Application Publication No. 2008/0107861, filed Nov. 2, 2007 in the name of Dalal, et al; and U.S. Patent Application Publication No. 2005/0177127, filed Jan. 28, 2005 in the name of Ashton, et al. Exemplary cohesive compounds include water-based polychloroprene emulsions, water-based polyurethanes inherently capable of crystallization (such as polyester polyurethane and polycaprolactone polyurethane), latex, polyisoprene, polystyrene-polyisoprene-polystyrene or polystyrene-polybutadiene-polystyrene elastomers, budadiene-acrylonitrile-iosoprene, butadiene-acrylonitrile polymers, poly(ethylene terephthalate), polyamide, polypropylene, polyethylene, and combinations thereof.

To prevent damage to chassis 12 when opening seal 38, the selective adhesive or cohesive used may be selected to exhibit peel forces between about 0.5N to about 15N. In some embodiments, the selective adhesive or cohesive will exhibit a peel force of less than about 10N. It should be understood that the magnitude of the strength of the bond created by the selective adhesive or cohesive along seal 38 may vary with the materials and construction of chassis 12, as different chassis designs will be more or less sensitive to damage from opening seal 38 at various peel forces. "Damage" refers to pinholes, tears, cuts, necking, or other unintended modifications of chassis 12 resulting from the force applied to open seal 38 which can or do degrade the performance of chassis 12. For example, some kinds of damage may permit leakage of urine or other exudates from chassis 12 when absorbent article 42 is used, or may interfere with proper fit of absorbent article 42 with undesirable effects on wearer comfort or aesthetics.

In some embodiments, seal 38 can be formed by melting at least a segment of the outer perimeters, or at least a segment proximate to the outer perimeters, of first and second portions 20 and 22 together using a suitable heating or melting device. Other suitable seals and/or methods of sealing are within the scope of the present disclosure, including, but not limited to ultrasonic seals and static charges. Such bonds may be constructed to permit opening seal 38 without damaging the product. For example, the bonds may be placed as discrete spot bonds, or may use a minimal amount of energy to tack the surfaces together without forming a bond of sufficient strength to damage chassis 12. A separate waist seal 36 may be used to join opposing lateral end portions 25 of first waist region 24 and opposing lateral end portions 29 of second waist region 27 to form a waist within absorbent article 42.

Figure 11A:
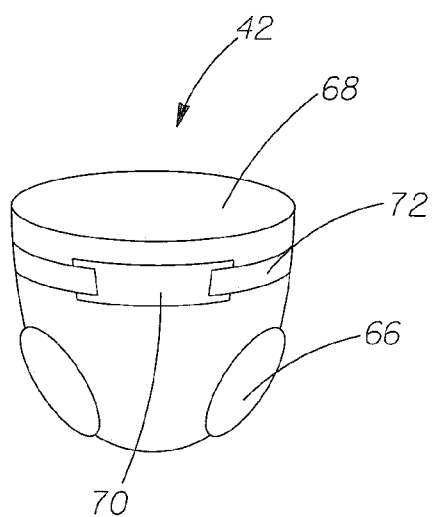
FIG. 11A is a perspective view of a taped-diaper configuration for an absorbent article.
Figure 11B:
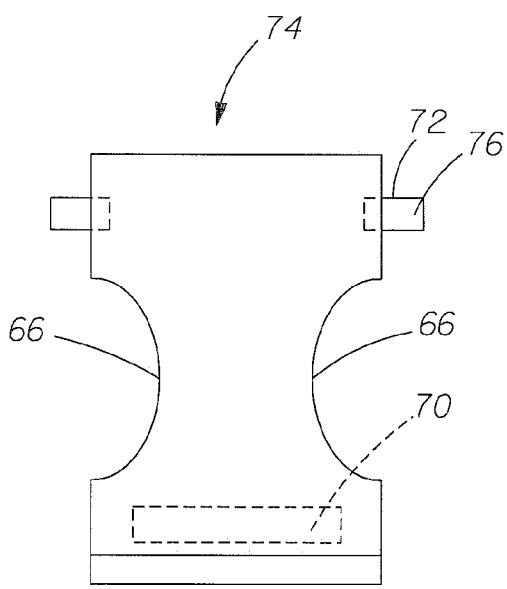
FIG. 11B is a perspective view of an open chassis of a taped diaper configuration for an absorbent article.
Figure 12:
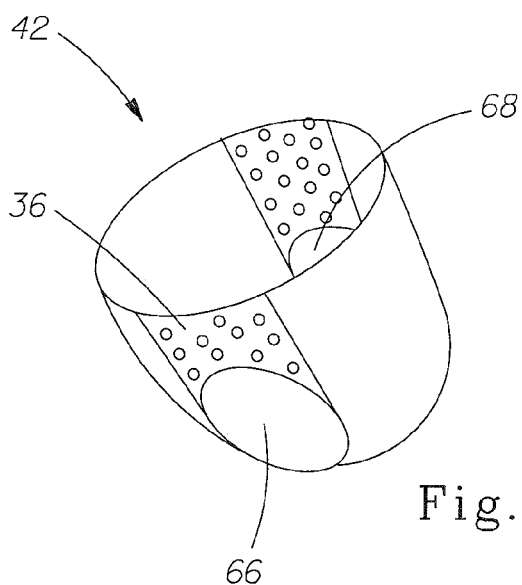
FIG. 12 is a side view of a pull-on style absorbent article.

In some embodiments, seals 36 (if present) and 38 may both be disrupted and separated and the absorbent article laid flat, thereby forming open chassis 74 which can be applied to a wearer in a taped diaper configuration. A taped diaper configuration may have a fastening system comprising, for example, fastening tab 72 and landing zone 70. Fastening tab 72 includes fastener 76. Fastener 76 may attach directly to backsheet 16, as, for example, if fastener 76 was an adhesive. Fastener 76 may also attach preferentially or exclusively to landing zone 70. For example, fastener 76 may comprise hooks and landing zone 70 may comprise loops, forming a hook-and-loop fastening system. Fastener 76 and, if present, landing zone 70, may be any fastener known in the art, including, but not limited to, adhesives, selective adhesives, cohesives, hook-and-loop, snaps, tab-and-slot, and the like. The fastening system may initially be engaged or unengaged. If the fastening system is engaged, once seal 38 is disrupted, the fastening system will hold the absorbent article in a pull-on configuration, as shown in FIG. 12. If the fastening system is unengaged, once seal 38 is disrupted, open chassis 74 is formed and can be applied to a wearer in a taped diaper configuration, as shown in FIGS. 11A and 11B. Alternatively, seal 38 may extend only partially along the perimeter at or adjacent to lateral end edge 30 and longitudinal side edges 32 and 34, such that when seal 38 is disrupted separate seal 36 remains intact, such that waist opening 68 and leg openings 66 are formed, thereby providing a pull-on style absorbent article (i.e. the product has a closed waist circumference and closed leg circumferences). A pull-on style absorbent article may also comprise a fastening system, to supplement or strengthen seal 36, or to provide a refastenable waist joint if seal 36 is disrupted. Seal 36 might be disrupted accidentally during application, or intentionally after absorbent article 42 has been applied to a wearer to remove absorbent article 42 to allow the wearer to use the toilet, or to check whether absorbent article 42 has been soiled, for example.

Figure 6:
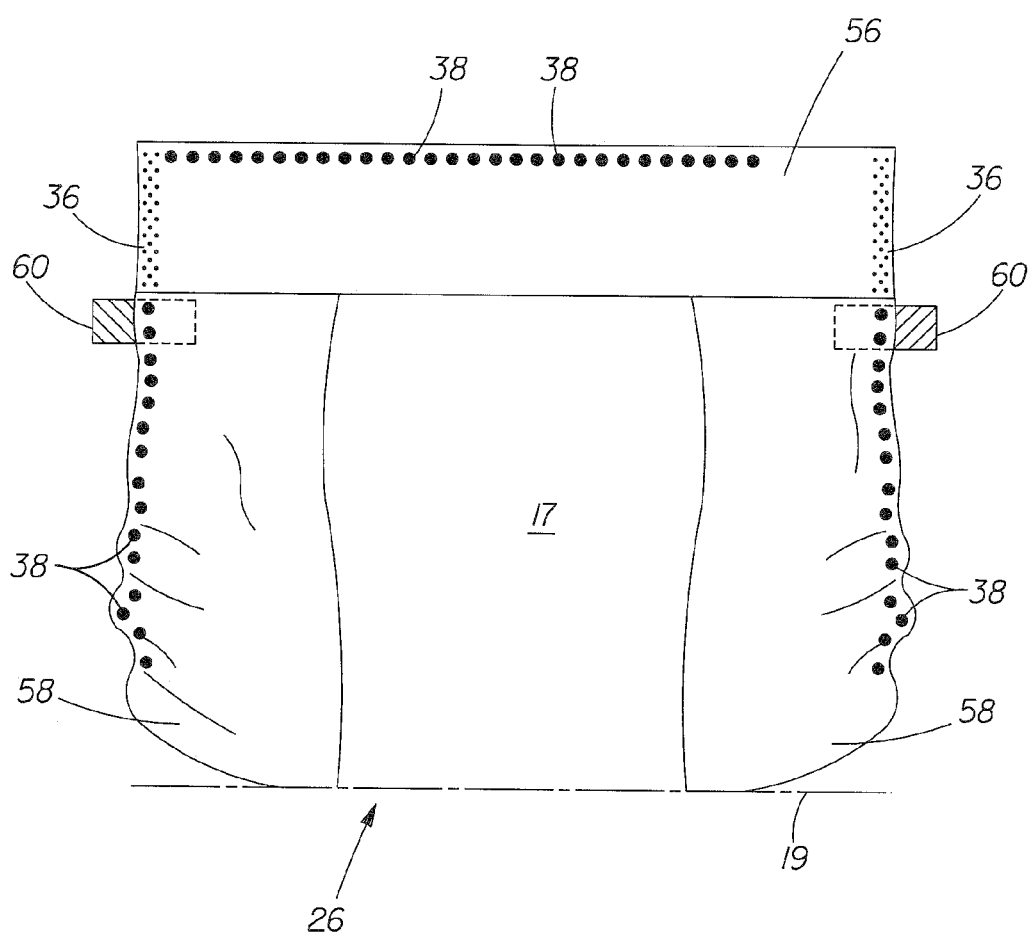
FIG. 6 is a view of the absorbent product of FIG. 5 showing mechanisms for disrupting the various seals.

Absorbent article 42 may have a grip or loose edge such that a caregiver or wearer can easily grasp and pull apart the sides of absorbent article 42 when the caregiver or wearer is ready to use absorbent article 42. There are a variety of ways to construct absorbent article 42 to facilitate opening seal 38, as shown in FIG. 6. For example, seal 38 may be placed such that corner 56 is not sealed, so that an edge of front waist portion and rear waist portion may be separately gripped and pulled apart to dislodge seal 38. In some embodiments, seal 38 may not extend fully to lateral axis 19 in crotch region 26, such that a finger or object may be inserted into opening 58 between seal 38 and lateral axis 19 and used to pull apart seal 38. In some embodiments, separate tab or grip 60 may be attached to facilitate opening seal 38.

Figure 7A:
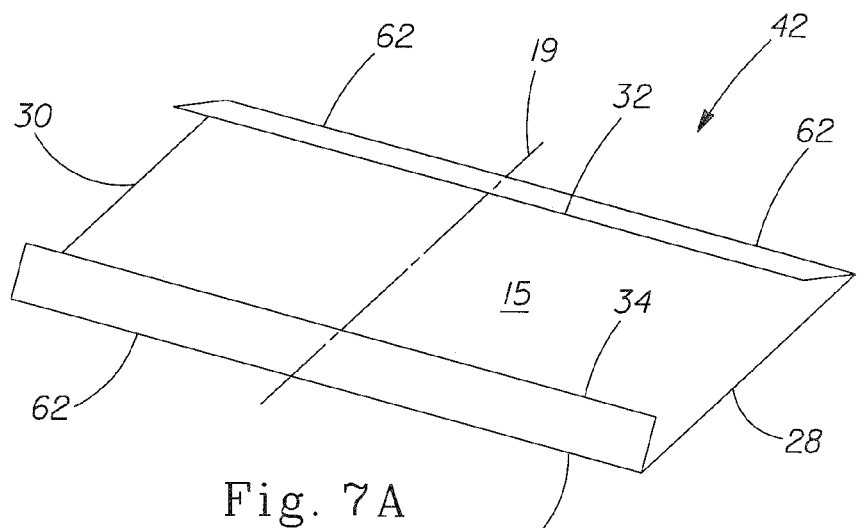
Figure 7B:
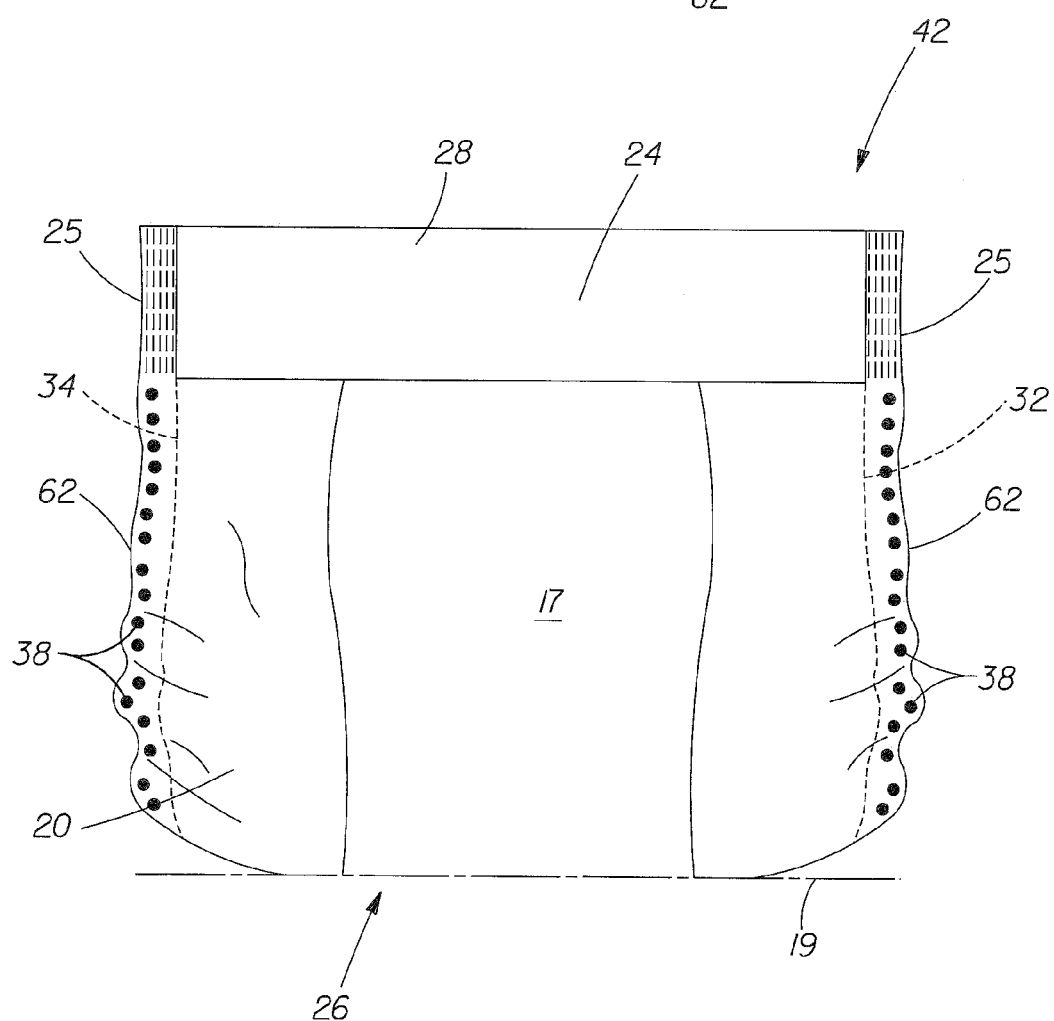
FIG. 7B is a front view of an absorbent product showing the position of various seals inboard of folded-in longitudinal edges.

In some embodiments, longitudinal side edges 32 and 34 may be folded inboard, creating fold lines 62, as shown in FIG. 7A. Fold lines 62 may be the outboard-most edges of crotch region 26 of absorbent article 42 once the article is folded. Folding may be mechanically guided during manufacture. In embodiments including leg cuffs and leg elastics or similar structures, folding may occur with or without mechanical guidance, as the article may tend to fold in on itself when the elastic elements in the article are released from tension and allowed to contract. Seal 38 may be somewhat laterally inboard of fold lines 62, such that fold lines 62 are themselves grips that can be used to open seal 38. In some embodiments, multiple grips or openings may be available to facilitate opening seal 38.

Seal 38 may provide different functionality in different embodiments. For example, in some embodiments, seal 38 may have intermittent or discrete bonding points. In such embodiments, seal 38 would prevent some contamination, but would not present a water-tight seal. In some embodiments, seal 38 may be a continuous seal, to provide greater protection against contamination by solid contaminants and some vapor-phase contaminants. Seal 38 may also be a continuous, water-tight seal. Where seal 38 presents a water-tight seal, and backsheet 16 is liquid impervious, absorbent article 42 would be protected from vapor and liquid contaminants as well as particulates and pests. A watertight seal may be particularly helpful in wet climates or environments, where absorbent article 42 would be exposed to more than typical humidity ("typical" humidity is approximately 40-60% relative humidity). Examples of wet climates or environments may include, but are not limited to, tropical climates, rainy or wet seasons, water parks, boats, and the like.

Figure 10:
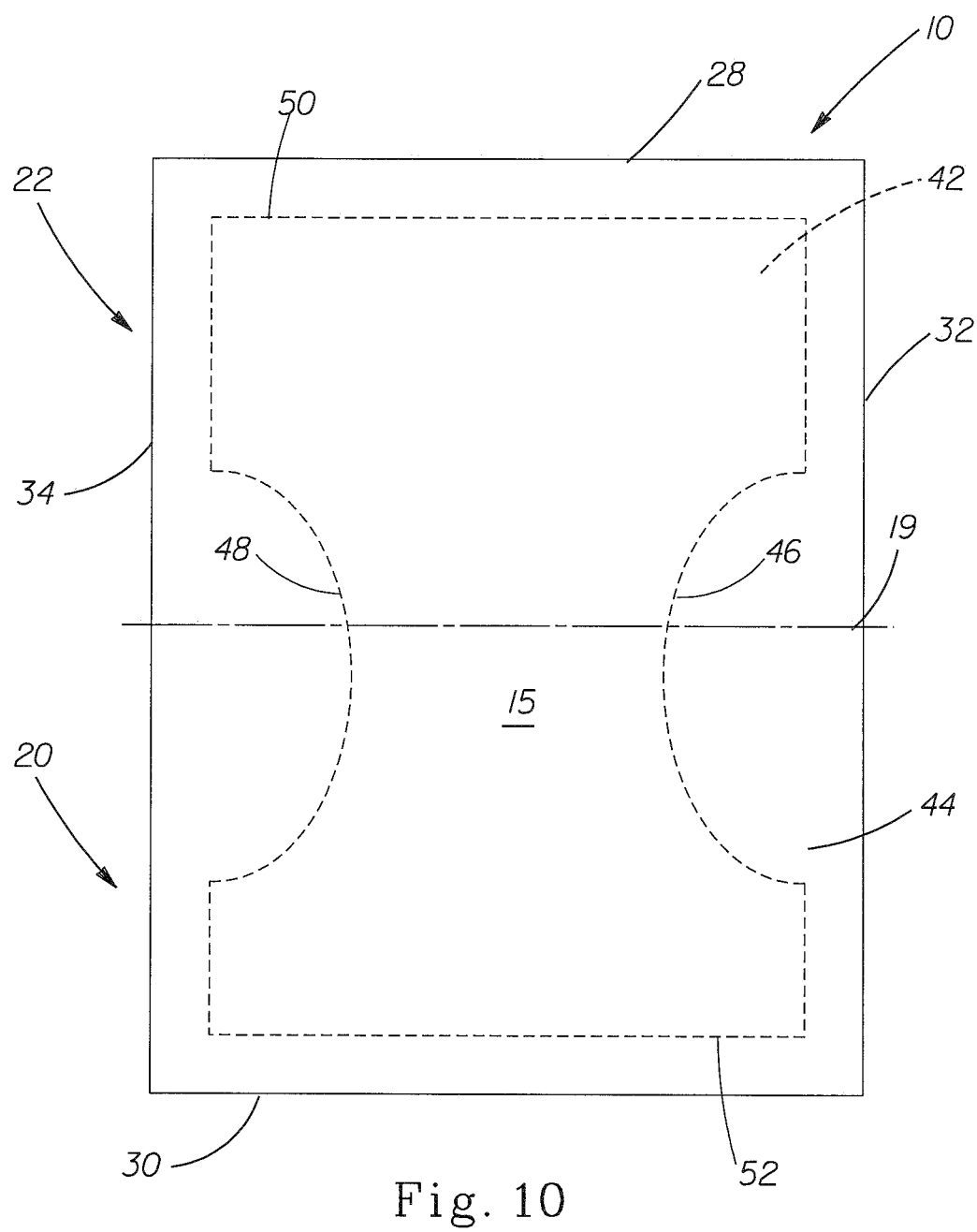
FIG. 10 is a plan view of an absorbent product having a removable trim region.

Absorbent article 42 may be derived from absorbent product 10 by manipulating absorbent product 10 before applying absorbent article 42 to a wearer. For example, as shown in FIG. 10, removable trim region 44 may be used to shape absorbent article 42 from absorbent product 10. For example, absorbent product 10 may be substantially rectangular, and absorbent article 42 may have a generally hourglass shape. An hourglass shape may be used to provide a trimmer fit through crotch region 26 of absorbent article 42, which may improve or create an impression of improved wearer comfort or mobility or both.

Figure 8:
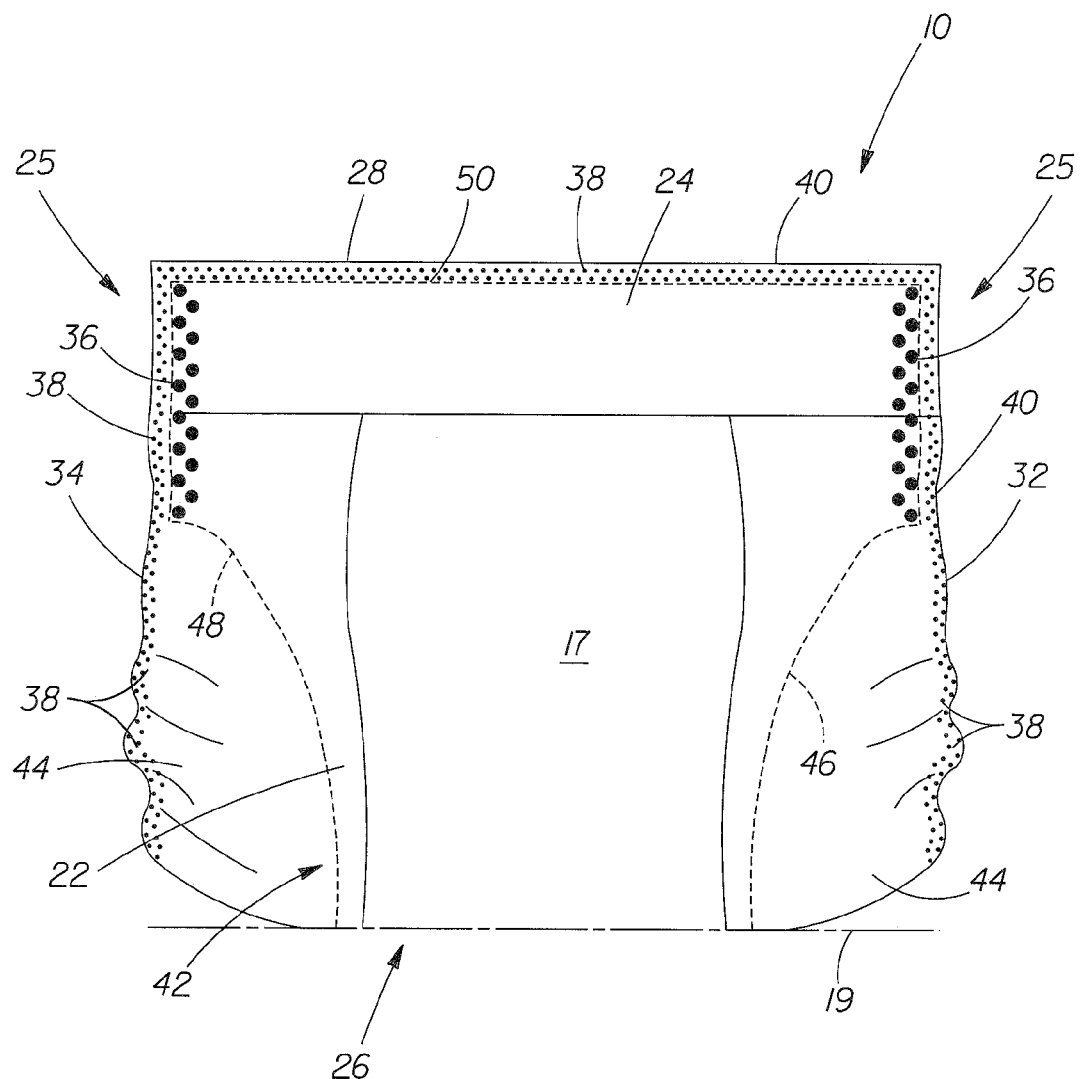
FIG. 8 is a front view of an absorbent product having a removable trim region.
Figure 9:
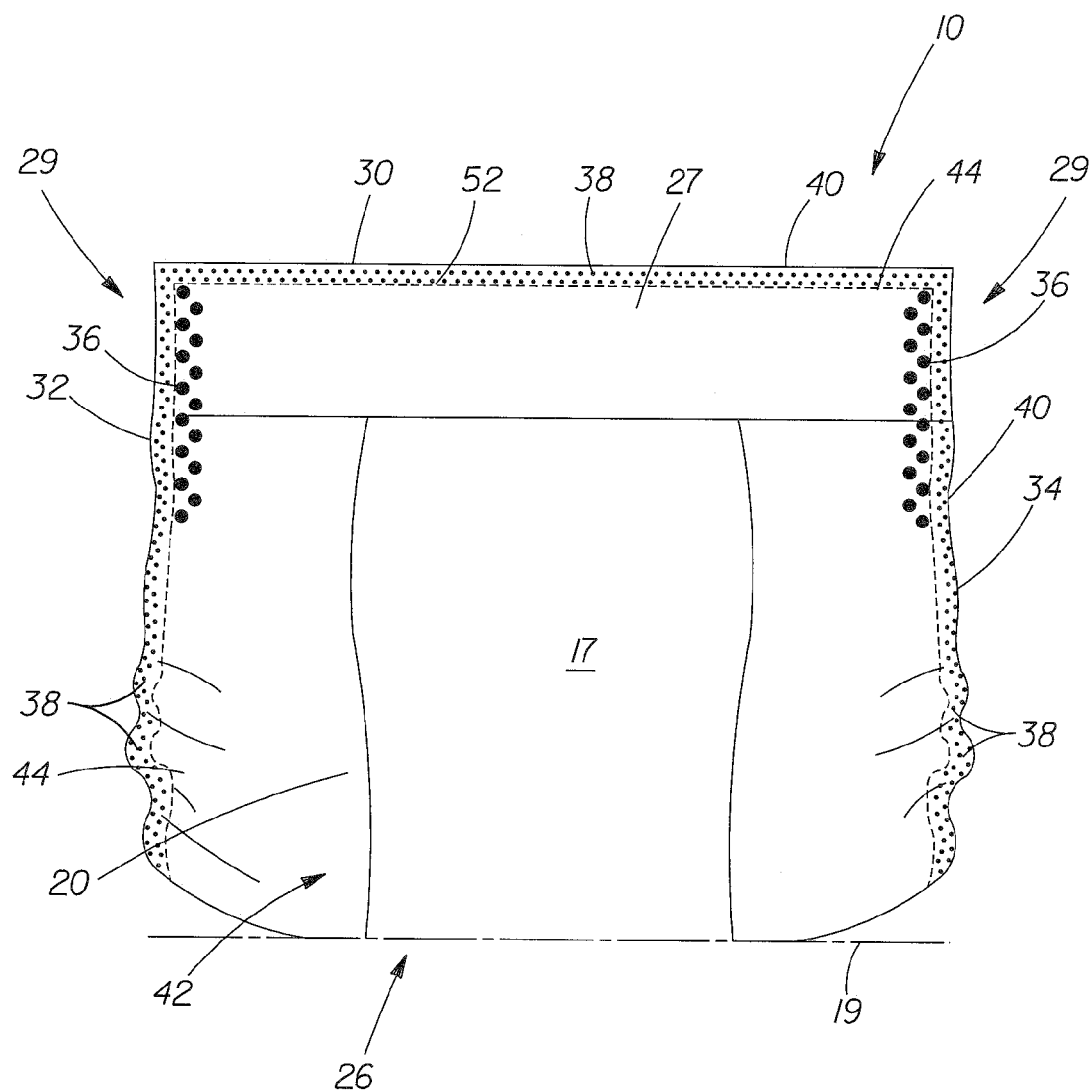
FIG. 9 is a rear view of an absorbent product having a removable trim region.

In various embodiments, longitudinal lines of weakness 46 and 48 and lateral lines of weakness 50 and 52 may be formed in absorbent product 10 such that removable trim region 44 can be separated from absorbent article 42 formed within absorbent product 10, as shown in FIGS. 8-10. Removable trim region 44 can comprise seal 38 thereon. Alternately, seal 38 may be inboard of removable trim region 44. Removable trim regions and methods of making them are disclosed in detail in a co-pending U.S. patent application, filed Nov. 24, 2009, entitled "ABSORBENT ARTICLES AND METHODS FOR MANUFACTURING THE SAME" and identified as attorney docket number 11516.

Removable trim region 44 may have an area formed between an outer perimeter of absorbent article 42, first and second longitudinal side edges 32 and 34, and first and second lateral end edges 28 and 30. Removable trim region 44 can be configured to be separated from absorbent article 42 about lines of weakness formed in absorbent product 10. After removable trim region 44 is separated from absorbent article 42, removable trim region 44 can be discarded and absorbent article 42 can be positioned on the wearer. In some embodiments, removable trim region 44 may comprise a portion of backsheet 16. In some embodiments, removable trim region 44 may comprise a portion of top sheet 14, a portion of backsheet 16, and/or a portion of absorbent core 18. Removable trim region 44 may have lines of weakness defined therein such that it can be readily separated from absorbent article 42 in portions or sections. Although FIG. 10 shows lines of weakness that are substantially symmetrical about lateral axis 19, lines of weakness may be constructed to shape first portion of chassis 20 and second portion of chassis 22 differently. For example, lines of weakness may be constructed asymmetrically about lateral axis 19 to provide greater coverage in the rear of absorbent article 42 and wider leg holes in crotch region 26 of absorbent article 42, to improve wearer comfort and exudate containment, as shown in FIGS. 8-9.

In one embodiment, a method for manufacturing absorbent product 10 may comprise the steps of advancing a continuous substrate through a converting line and combining the substrate with topsheet 14 and absorbent core 18. In such an embodiment, absorbent core 18 may be disposed between topsheet 14 and the substrate. In some embodiments, the substrate may then be cut to form backsheet 16 having first lateral end edge 28, second lateral end edge 30, first longitudinal side edge 32, and second longitudinal side edge 34. Backsheet 16, absorbent core 18, and topsheet 14 may then be folded about lateral axis 19 to position first lateral end edge 28 adjacent to, or substantially adjacent to, second lateral end edge 30, to position first portion 20 of first longitudinal side edge 32 adjacent to, or substantially adjacent to, second portion 22 of first longitudinal side edge 32, and to position first portion 20 of second longitudinal side edge 34 adjacent to, or substantially adjacent to, second portion 22 of second longitudinal side edge 34.

After such positioning, first lateral end edge 28 may be connected to second lateral end edge 30, first portion 20 of first longitudinal side edge 32 may be connected to second portion 22 of first longitudinal side edge 32, and first portion 20 of second longitudinal side edge 34 may be connected to second portion 22 of second longitudinal side edge 34. The connection between the various portions may comprise a seal, such as a selective adhesive or cohesive seal, for example.

First longitudinal line of weakness 46, if present, may be created laterally inboard of first longitudinal end edge 32, second longitudinal line of weakness 48 may be created laterally inboard of second longitudinal end edge 34, first lateral line of weakness 50 may be created longitudinally inboard of first lateral end edge 28, and second lateral line of weakness 52 may be created longitudinally inboard of second lateral end edge 30. In some embodiments, the various lines of weakness may define outer perimeter 40 of absorbent article 42 comprising absorbent core 18 disposed between backsheet 16 and topsheet 14. Removable trim region 44 may be defined by an area of backsheet 16 between outer perimeter 40 of absorbent article 42 and first and second longitudinal side edges 32, 34 and first and second lateral end edges 28, 30.

In some embodiments, absorbent article 42 may comprise a diaper having wearer facing surface 15 defined by topsheet 14 and garment facing surface 17 defined by backsheet 16. Absorbent article 42 may have longitudinally opposing first and second waist regions 24, 27 adjacent to, or substantially adjacent to, first and second lateral lines of weakness 50, 52, and crotch region 26 longitudinally intermediate of first and second waist regions 27, 27. Opposing lateral end portions 25 of first waist region 24 may be connected with opposing lateral end portions 29 of second waist region 27 to form waist opening 68. In some embodiments, the connection between first and second waist regions 24, 27 may comprise overlap seams or butt seams, for example. In some embodiments, first and second longitudinal lines of weakness 46, 48 may define leg openings 66 in absorbent article 42. In an embodiment where absorbent article 42 comprises ears, first and second ears may be connected to first waist region 24. The first and second ears may be configured to releasably connect to second waist region 27, or ears formed thereon, to form waist opening 68 in absorbent article 42.

In some embodiments, the various lines of weakness may be formed in backsheet 16, topsheet 14, and/or absorbent core 18 by perforating backsheet 16, topsheet 14, and/or absorbent core 18 using a perforating device or a cutting member, for example. In other embodiments, the various lines of weakness may be formed in backsheet 16, topsheet 14, and/or absorbent core 18 by scoring backsheet 16, topsheet 14, and/or absorbent core 18 using a scoring device, for example. In one embodiment, first and second lateral lines of weakness 50, 52 may be connected to or can intersect with first and second longitudinal lines of weakness 46, 48.

In some embodiments, first portion 20 of absorbent product 10 and second portion 22 of absorbent product 10 may be sealed to each other within the area of removable trim region 44, or, in other embodiments, may be sealed to each other outside the areas of removable trim regions 44. In some embodiments, portions of seal 38 are within area of removable trim 44 and other portions of seal 38 are outside areas of removable trim 44. In some embodiments, an entire length of first lateral end edge 28 may be sealed with an entire length of second lateral end edge 30; an entire length of first portion 20 may be sealed with an entire length of second portion 22 of first longitudinal side edge 32; and an entire length of first portion 20 may be sealed with an entire length of second portion 22 of second longitudinal side edge 34. In other embodiments, seal 38 may be intermittent along various portions of perimeter 40 of absorbent article 42. In such an embodiment, intermittent seal 38 can join first portion 20 of absorbent product 10 with second portion 22 of absorbent product 10 such that wearer facing surface 15 of absorbent article 42 can remain in a sanitary condition prior to use of absorbent article 42.

Absorbent products 10 according to the present disclosure may be further processed or packaged to facilitate individual sales. For example, absorbent product 10 may be further folded along second lateral axis 64, shown in FIG. 5, to reduce the length of absorbent product 10. A small amount of selective adhesive or cohesive may be placed on garment-facing side 17 of backsheet 16 to help maintain absorbent product 10 in a bi-folded position. Absorbent product 10 may be folded along additional lateral and/or longitudinal axes (not shown) to further reduce perimeter 40 of the folded product, as desired. One or more absorbent products 10 intended for individual sale may be placed in a bulk package for convenient shipping and for convenient handling and storage. For example, 5, 10, 12, 15, 20 or more absorbent products may be stacked together and placed in a box, plastic overwrap, or other packaging. A retailer or purchaser may then remove individual units from the bulk package as desired. The bulk packaging may be designed to help keep the absorbent products clean, dry, and neatly folded until sale. For example, the bulk packaging may provide an opening that encourages or facilitates the removal of a single individual product at a time, such that absorbent products are not scattered, shuffled, dropped, or otherwise handled when an individual unit is removed from the bulk packaging.

Because the overwrap or packaging is not necessarily conveyed to the consumer or user of the product, individual absorbent products may have printing on backsheet 16 or visible through backsheet 16. For example, individual absorbent products 10 may be printed with brand images such as the trade name or trade mark for the product, or with indicia useful to the consumer or user, such as the size or variety of the absorbent article (such as Small, Medium, Large, Sensitive, Overnight Protection, Diaper Rash Prevention, etc.), or with instructions for using absorbent product 10. For example, removable trim region 44 may be printed with instructions for removing the trim region, or tab 60 may be printed with instructions for opening seal 38. Methods and materials for printing on individual absorbent products 10 are well known in the art, and may be selected for compatibility with the materials and construction of chassis 12. Printing methods and materials may be selected which will withstand high moisture or water exposure, or the printing may be disposed on a layer subjacent to and visible through backsheet 16, particularly, but not exclusively, in embodiments of absorbent product 10 intended to provide a watertight barrier to contaminants.

Individual absorbent products 10 may be provided with individual overwraps, boxing, or other packaging. Although seal 38 and/or removable trim region 44 are configured to protect wearer-facing surface 15 from contamination, the exposed portions of backsheet 16 would still be susceptible to contamination and damage, particularly if the absorbent products are roughly handled or stored for an extended period of time. Using the embodiments of the present disclosure, even if an overwrap is desired, it may be possible to use a thinner, less robust overwrap, since wearer-facing surface 15 of absorbent article 42 is already protected. Thus, the present disclosure may allow for using thinner materials or using less robust materials for individual overwraps, which may in turn allow for improvements in environmental impact (less overall material disposed, less overall weight to be transported, ability to use less robust biodegradable or recyclable overwrap materials instead of new, petroleum-derived plastics) or reduced cost (less overall material, less robust materials).

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

What is claimed is:

1. An absorbent product comprising a chassis comprising:
   a topsheet having a wearer-facing surface;
   a backsheet having a garment-facing surface;
   an absorbent core disposed between the topsheet and the backsheet;
   a first longitudinal side edge, a second longitudinal side edge, a first lateral end edge, a second lateral end edge, a first waist region comprising laterally opposed ends, a second waist region comprising laterally opposed ends, a crotch region longitudinally intermediate the first and second waist regions, and a first lateral axis,
   wherein the absorbent product is folded about the first lateral axis such that the first waist region and the second waist region are in a facing relationship,
   wherein the laterally opposed ends of the first waist region are joined with the laterally opposed ends of the second waist region at first and second joints to form a waist opening and first and second leg openings, wherein the first and second joints are not intended to be broken during use of the absorbent product,
   wherein a first seal seals the waist opening, wherein the first seal extends between the laterally opposed ends of the first and second waist regions,
   wherein a second seal seals the first leg opening,
   wherein a third seal seals the second leg opening, wherein the first, second, and third seals are frangible.

2. The absorbent product of claim 1, wherein the first, second, and third seals are formed using a cohesive.

3. The absorbent product of claim 1, wherein the first, second, and third seals are formed using a selective adhesive.

4. The absorbent product of claim 1, wherein at least a portion of the first, second, or third seals comprises discrete, intermittent bonding points.

5. The absorbent product of claim 1, wherein at least a portion of the first, second, or third seals comprises a continuous seal.

6. The absorbent product of claim 1, wherein the first, second, and third seals are watertight.

7. The absorbent product of claim 1, wherein the second or third seal does not extend completely to the first lateral axis.

8. The absorbent product of claim 1, wherein the first and second longitudinal side edges are folded inboard, creating outboard fold edges, and the second and third seals are disposed inboard of the fold edges and outboard of the first and second longitudinal side edges, when the absorbent product is folded.

9. The absorbent product of claim 1, further comprising a second lateral axis, wherein the first portion of the chassis is folded about the second lateral axis.

10. The absorbent product of claim 1, further comprising a removable trim region.

11. The absorbent product of claim 10, wherein the removable trim region is substantially symmetrical about the first lateral axis.

12. The absorbent product of claim 10, wherein the removable trim region is asymmetrical about the first lateral axis.

13. The absorbent product of claim 10, wherein the removable trim region is inboard of the second and third seals.

14. The absorbent product of claim 10, wherein the removable trim region is outboard of the second and third seals.

15. The absorbent product of claim 1, further comprising an overwrap.

16. The absorbent product of claim 1, wherein the first, second, and third seals each exhibit a peel force between 0.5N and 10N.

17. The absorbent product of claim 16, wherein the backsheet material can withstand a peel force greater than the peel force of each of the first, second, and third seals.

18. The absorbent product of claim 1, wherein the first seal does not extend completely to one corner of the lateral end edges.

19. The absorbent product of claim 1, wherein the absorbent product comprises laterally opposing ends joined together to form a waist, and the second and third seals do not overlap the laterally opposing ends.

20. An absorbent product comprising a chassis comprising a topsheet, backsheet, and an absorbent core sandwiched between the topsheet and the backsheet, wherein the chassis further comprises:
    a first waist region comprising laterally opposed ends;
    a second waist region comprising laterally opposed ends;
    a crotch region longitudinally intermediate the first and second waist regions; and
    a lateral axis,
    wherein the absorbent product is folded about the lateral axis such that the first waist region and the second waist region are in a facing relationship,
    wherein the laterally opposed ends of the first waist region are joined with the laterally opposed ends of the second waist region at first and second joints to form a waist opening and first and second leg openings, wherein the first and second joints are not intended to be broken during use of the absorbent product,
    wherein the waist opening is sealed by a first seal, the first leg opening is sealed by a second seal, and the second leg opening is sealed by a third seal, wherein the first seal extends between the laterally opposed ends of the first and second waist regions, wherein the first, second, and third seals are frangible.

* * * * *